(12) United States Patent
Yang et al.

(10) Patent No.: US 8,808,229 B2
(45) Date of Patent: Aug. 19, 2014

(54) SYSTEM AND METHOD OF WIRELESS PHYSIOLOGICAL SIGNAL INTEGRATION

(75) Inventors: Yuh-Shyong Yang, Hsinchu (TW); Ming-Yu Lin, Hsinchu (TW); Kuei-Shin Tsai, Taichung (TW); Wen-Ying Chang, Bade (TW); Chih-Heng Lin, Tainan (TW); Jo-Fen Wei, Hsinchu County (TW)

(73) Assignee: National Applied Research Laboratories, Taipei (TW)

( * ) Notice: Subject to any disclaimer, the term of this patent is extended or adjusted under 35 U.S.C. 154(b) by 940 days.

(21) Appl. No.: 12/291,876

(22) Filed: Nov. 14, 2008

(65) Prior Publication Data
US 2009/0137947 A1 May 28, 2009

(30) Foreign Application Priority Data

Nov. 27, 2007 (TW) .............................. 96145052 A

(51) Int. Cl.
| | |
|---|---|
| *A61M 31/00* | (2006.01) |
| *A61B 5/00* | (2006.01) |
| *G06F 19/00* | (2011.01) |
| *A61B 5/021* | (2006.01) |
| *A61B 5/145* | (2006.01) |
| *A61B 5/024* | (2006.01) |
| *A61B 5/1486* | (2006.01) |
| *A61B 5/0476* | (2006.01) |

(52) U.S. Cl.
CPC ........... *A61B 5/4839* (2013.01); *A61B 5/14532* (2013.01); *A61B 5/02438* (2013.01); *A61B 5/0002* (2013.01); *A61B 5/145* (2013.01); *G06F 19/3468* (2013.01); *A61B 5/14865* (2013.01); *A61B 5/1486* (2013.01); *A61B 5/0476* (2013.01); *A61B 5/0006* (2013.01); *A61B 5/021* (2013.01)
USPC ............................................. 604/66; 600/345

(58) Field of Classification Search
USPC ............................................. 604/66–67, 503
See application file for complete search history.

(56) References Cited

U.S. PATENT DOCUMENTS

| | | | |
|---|---|---|---|
| 5,860,957 A | 1/1999 | Jacobsen et al. | |
| 5,862,803 A * | 1/1999 | Besson et al. | 600/508 |
| 6,175,752 B1 * | 1/2001 | Say et al. | 600/345 |
| 6,464,687 B1 * | 10/2002 | Ishikawa et al. | 604/891.1 |
| 6,929,636 B1 | 8/2005 | von Alten | |
| 2004/0249227 A1 * | 12/2004 | Klapproth et al. | 585/250 |
| 2006/0281067 A1 * | 12/2006 | Simpson et al. | 435/4 |

* cited by examiner

*Primary Examiner* — Nicholas Lucchesi
*Assistant Examiner* — Melissa A Snyder
(74) *Attorney, Agent, or Firm* — Haverstock & Owens LLP

(57) ABSTRACT

A system of a wireless physiological signal integration is provided. The system includes a wireless transmission sensor chip and a drug delivering system, wherein the wireless transmission sensor chip includes a sensor sensing a physiological signal of a patient, a signal conversion module converting the physiological signal into a converted signal, and a wireless transmission module wirelessly transmitting the converted signal, and the drug delivering system determines a dose of a drug and a timing for providing the drug according to the converted signal.

15 Claims, 4 Drawing Sheets

SYSTEM AND METHOD OF WIRELESS PHYSIOLOGICAL SIGNAL INTEGRATION

FIELD OF THE INVENTION

The present invention relates to a system and method of physiological signal integration, and more particularly to a system and method of wireless physiological and biochemical signal integration.

BACKGROUND OF THE INVENTION

Currently, most apparatuses for detecting a patient's physiological signals are respectively connected to a monitoring device through conducting wires fastened on the patient. The detected physiological parameters are output through the conducting wires and displayed on the screen of the monitoring device. These detected physiological parameters are usually written on a paper form by a nurse when she doing the regular nursing round, and then provided for a doctor to do the analysis and diagnosis. Such a method can not provide an instant and continuous monitoring, and it might result in an erroneous diagnosis or delay the timing for therapy.

In addition, these conducting wires connected to the patient's body cause a great inconvenience when the nurse needs to clean the patient's body or assist the patient to turn over his/her body. Because the conducting wires are connected to the detecting apparatuses, when the patient needs to change the sickroom or do some specific examinations, such as MRI, the apparatuses must move together with the patient, or the conducting wires must be removed from the patient. Therefore, it is difficult to keep monitoring the patient's physiological status.

Moreover, a dose of a drug is calculated according to some parameters, such as the patient's age, body weight, gender, etc., and then the drug will be delivered to the patient regularly. However, each patient has different symptom, physiological status, and metabolism rate, and the calculating standards are usually adapted to Western people but not Asians. Thus, such a method for determining the dose of the drug and regularly delivering the drug is not appropriate.

From the above description, it is necessary to provide a system and method of wireless physiological signal integration, so that patients can get rid of the fetters of conducting wires, and the detected results can be integrated and transmitted to the doctor correctly for making the diagnosis. The system and method provided by the present invention further includes a drug delivering system for delivering the drug automatically based on the status of the patient, so as to determine the dose of the drug and the timing of providing the drug more precisely.

In order to overcome the drawbacks in the prior art, a system and method of wireless physiological signal integration is provided. The particular design in the present invention not only solves the problems described above, but also is easy to be implemented. Thus, the invention has the utility for the industry.

SUMMARY OF THE INVENTION

In accordance with one aspect of the present invention, a system of wireless physiological signal integration is provided to integrate the detected physiological signals and wirelessly transmit these signals, so that patients can get rid of the fetters of conducting wires, wherein the physiological signal include various physiological parameters including biochemical signals, such as biological molecules, such as DNA, protein, ions, RNA, etc. The system provided in the present invention further includes a drug delivering system for determining the dose of a drug and the timing to provide the drug.

In addition, the present invention also provides a method of wireless physiological signal integration to continuously monitor the physiological status and the concentration of biological molecules of a patient and automatically deliver a drug to the patient according to the patient's physiological status on the instant.

In accordance with another aspect of the present invention, a system of a wireless physiological signal integration is provided. The system includes a wireless transmission sensor chip and a drug delivering system, wherein the wireless transmission sensor chip includes a sensor sensing a physiological signal of a patient, a signal conversion module converting the physiological signal into a converted signal, and a wireless transmission module wirelessly transmitting the converted signal; the drug delivering system determining a dose of a drug and a timing for providing the drug according to the converted signal.

Preferably, the wireless transmission sensor chip is a System-on-Chip, where the sensor, the signal conversion module and the wireless transmission module is fabricated using an integrated process technology.

Preferably, the wireless transmission sensor chip is fabricated by an integrated circuit process.

Preferably, the integrated circuit process is a CMOS process.

Preferably, the wireless transmission sensor chip is one of an invasive chip implanted in the patient and a non-invasive chip fastened at an exterior of the patient.

Preferably, the wireless transmission sensor chip further includes a plurality of sensors for sensing a plurality of physiological signals.

Preferably, the sensor is one selected from a group consisting of a charge-induced transistor, a field effect transistor, an organic thin film transistor, an ion selective electrode, and a photodiode.

Preferably, the sensor further includes a reacting substance encapsulated by a sol-gel.

Preferably, the physiological signal is one selected from a group consisting of an electrical signal, a chemical signal and a physical signal.

Preferably, the sensor converts the physiological signal into a current and transmits the current to the signal conversion module when the physiological signal is one of the chemical signal and the physical signal, and the signal conversion module converts the current into an analog voltage and further converts the analog voltage into the converted signal, wherein the converted signal is an analog voltage signal.

Preferably, when the physiological signal is the electrical signal, the signal conversion module converts the electrical signal into an analog voltage and further converts the analog voltage into the converted signal, and the converted signal is an analog voltage signal.

Preferably, the physiological signal is one selected from a group consisting of a drug concentration, a DNA, an RNA, a protein, an ion, a blood sugar, a blood oxygen, a physiological substance, a brain wave, an electrocardiogram signal, a blood pressure, a pulse rate, a body temperature, and a light signal.

Preferably, the system further includes a power supply electrically connected to the wireless transmission sensor chip for providing a power thereto, wherein the power supply is a battery.

Preferably, the drug delivering system further includes a wireless signal receiving module for receiving the converted signal.

Preferably, the drug delivering system provides the drug to the patient automatically.

Preferably, the drug delivering system delivers the drug to a body part of the patient.

In accordance with a further aspect of the present invention, a method of a wireless physiological signal integration is provided. The method includes steps of sensing a physiological signal of a patient, converting the physiological signal into a converted signal, and wirelessly transmitting the converted signal to a drug delivering system.

Preferably, the method further includes steps of determining a dose of a drug and a timing for providing the drug by the drug delivering system, and providing the drug to the patient automatically.

Preferably, the converted signal is wirelessly transmitted through a medical wireless bandwidth.

Preferably, a frequency of the medical wireless bandwidth is 1.4 GHz.

In accordance with further another aspect of the present invention, a wireless transmission sensor chip is provided. The wireless transmission sensor chip includes a sensor sensing a physiological signal, a signal conversion module converting the physiological signal into a converted signal, and a wireless transmission module wirelessly transmitting the converted signal.

Additional objects and advantages of the invention will be set forth in the following descriptions with reference to the accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed.

Figure 1:
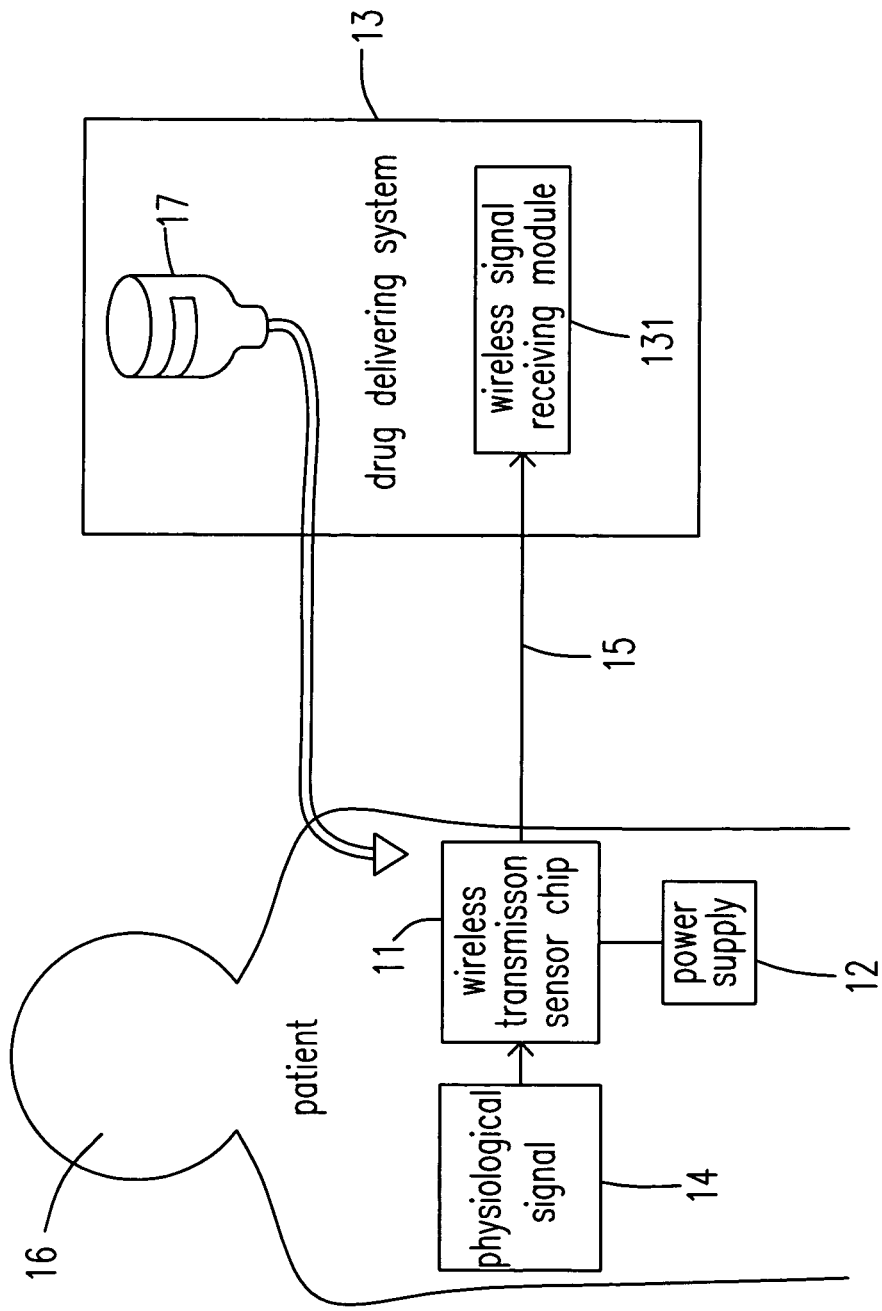
FIG. 1 is a schematic diagram of the system of a wireless physiological signal integration according to a preferred embodiment in the present invention.

Please refer to FIG. 1, which shows a schematic diagram of the system of wireless physiological signal integration according to a preferred embodiment in the present invention. The system includes a wireless transmission sensor chip 11, a power supply 12, and a drug delivering system 13, wherein the power supply 12 can be a battery electrically connected to the wireless transmission sensor chip 11 for providing a power thereto. The wireless transmission sensor chip 11 can be an invasive chip implanted in the skin of a patient 16, or can be a non-invasive chip fastened at the exterior of the body of the patient 16.

As shown in FIG. 1, the wireless transmission sensor chip 11 senses a physiological signal 14 of the patient 16, converts the physiological signal 14 into a converted signal 15, and wirelessly transmits the converted signal 15, wherein the converted signal 15 can be an analog voltage signal. The transmitted converted signal 15 is received by a wireless signal receiving module 131 of the drug delivering system 13 and analyzed thereby, so as to determine the physiological status of the patient 16 and provide a drug 17 to the patient 16. Besides, the drug 17 can be delivered to different body parts of the patient 16 simultaneously.

The physiological signal 14 can be any kind of physiological parameter, such as drug concentrations, blood sugar, blood oxygen, any other physiological substance, brain wave, electrocardiogram signals, blood pressure, pulse rate, body temperature, or light signals. The converted signal 15 is wirelessly transmitted through a medical wireless bandwidth with a frequency of 1.4 GHz.

Figure 2:
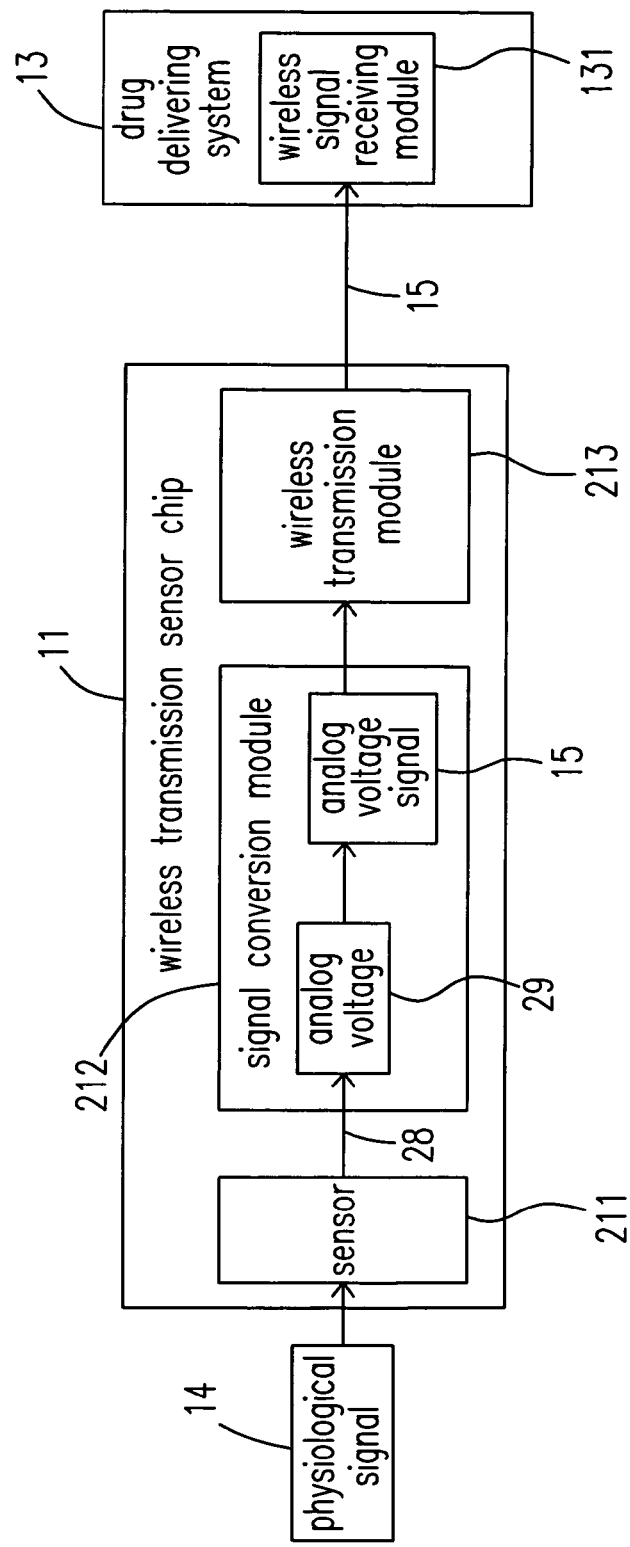
FIG. 2 is a schematic diagram showing the conversions of signals of the method of wireless physiological signal integration according to a preferred embodiment in the present invention.

Please refer to FIG. 2, which is a schematic diagram showing the conversions of signals of the method of wireless physiological signal integration according to a preferred embodiment in the present invention, wherein the wireless transmission sensor chip 11 is a System-on-Chip (SOC) fabricated by a Complementary Metal-Oxide-Semiconductor (CMOS) process. The wireless transmission sensor chip 11 includes a sensor 211, a wireless transmission module 213, and a signal conversion module 212 electrically connected to the sensor 211 and the wireless transmission module 213.

As shown in FIG. 2, when sensing a physiological signal 14, the sensor 211 of the wireless transmission sensor chip 11 converts the physiological signal 14 into a current 28 and transmits the current 28 to the signal conversion module 212. The signal conversion module 212 converts the current 28 into an analog voltage 29, and further converts the analog voltage 29 into a converted signal 15, wherein the converted signal 15 is an analog voltage signal 15 and will be transmitted to the wireless signal transmission module 213. After that, the analog voltage signal 15 is wirelessly transmitted by the wireless transmission module 213 and received by a wireless receiving module 131 of the drug delivering system 13, wherein the analog voltage signal 15 is transmitted through a medical wireless bandwidth with a frequency of 1.4 GHz.

The physiological signal 14 might be an electrical signal, a chemical signal or a physical signal. When the physiological signal is a chemical signal or a physical signal, the sensor 211 converts the physiological signal 14 into a current 28 and transmits the current 28 to the signal conversion module 212, and the signal conversion module 212 converts the current 28 into an analog voltage 29 and further converts the analog voltage 29 into the analog voltage signal 15. On the other hand, when the physiological signal 14 is an electrical signal, the electrical signal is regarded as the current 28 and directly transmitted to the signal conversion module 212. The signal conversion module 212 will convert the current 28 into an analog voltage 29 and further convert the analog voltage 29 into the analog voltage signal 15 in the same way.

Figure 3:
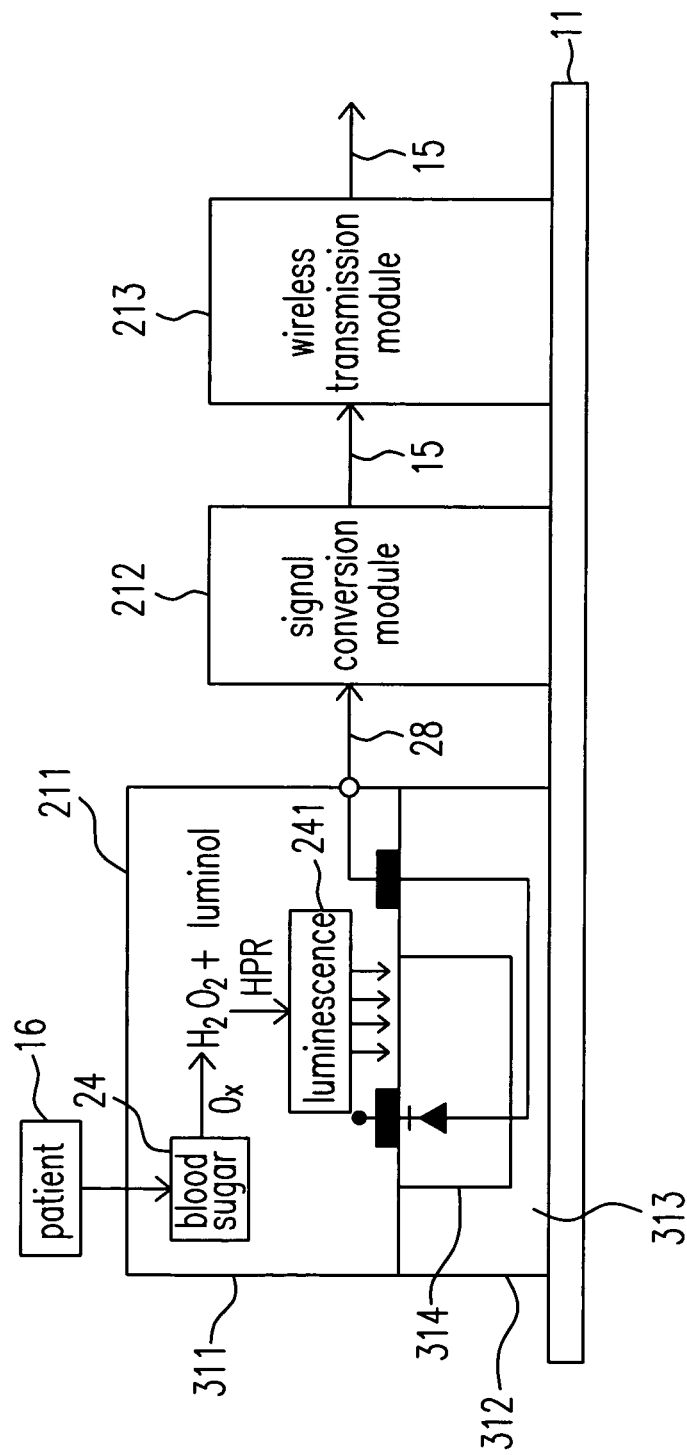
FIG. 3 is a schematic diagram of the wireless transmission sensor chip according to a preferred embodiment in the present invention.

Please refer to FIG. 3, which shows schematic diagram of the wireless transmission sensor chip according to a preferred embodiment in the present invention, wherein the wireless transmission sensor chip 11 is a SOC fabricated by a CMOS process. The wireless transmission sensor chip 11 includes a sensor 211, a wireless transmission module 213, and a signal conversion module 212 electrically connected to the sensor 211 and the wireless transmission module 213. In addition, the sensor 211 further includes a reaction area 311 and a light sensor 312, wherein reaction area 311 contains a glucose oxidase (Ox), a peroxidase (HPR), and a luminescent substance (luminol); the glucose oxidase (Ox), the peroxidase (HPR), and the luminescent substance (luminol) are encapsulated by a sol-gel technique. The light sensor 312 is a P-N junction photodiode including an $N^+$ diffusion layer 314 and a P matrix 313.

As shown in FIG. 3, when a blood sugar 24 of a patient 16 enters the reaction area 311 of the sensor 211, the blood sugar 24 is catalyzed by the glucose oxidase (Ox) to generate peroxide ($H_2O_2$). The peroxide ($H_2O_2$) is catalyzed by the peroxidase (HPR) and reacts with the luminescent substance (luminol) to generate a luminescence 214. The luminescence 214 is detected by the light sensor 312 and a reversed biased is formed. The sensor 211 converts the reversed biased into a current 28 and transmits the current 28 to the signal conversion module 212. The signal conversion module 212 converts the current 28 into a converted signal 15 and transmits the converted signal 15 to the wireless transmission module 213 for wirelessly transmitting the converted signal 15.

Because the wireless transmission sensor chip 11 of the present invention is fabricated as a one-piece device by CMOS process, wherein a light sensing area of the light sensor 312 is only in a size of 0.5 mm×0.5 mm square. Thus, a miniaturization design of the wireless transmission sensor chip 11 can be achieved, and it can be easily fastened at a body part of the patient 16. Furthermore, because the reacting substances, including the enzyme used to catalyze the reaction of the physiological signal, i.e. the blood sugar 24, are encapsulated in the reaction area 311 upon the light sensor 312, the reaction results can be detected by the light sensor 312 immediately, so as to meet the requirements of the present invention for a rapid, instant and continuous detection.

Figure 4:
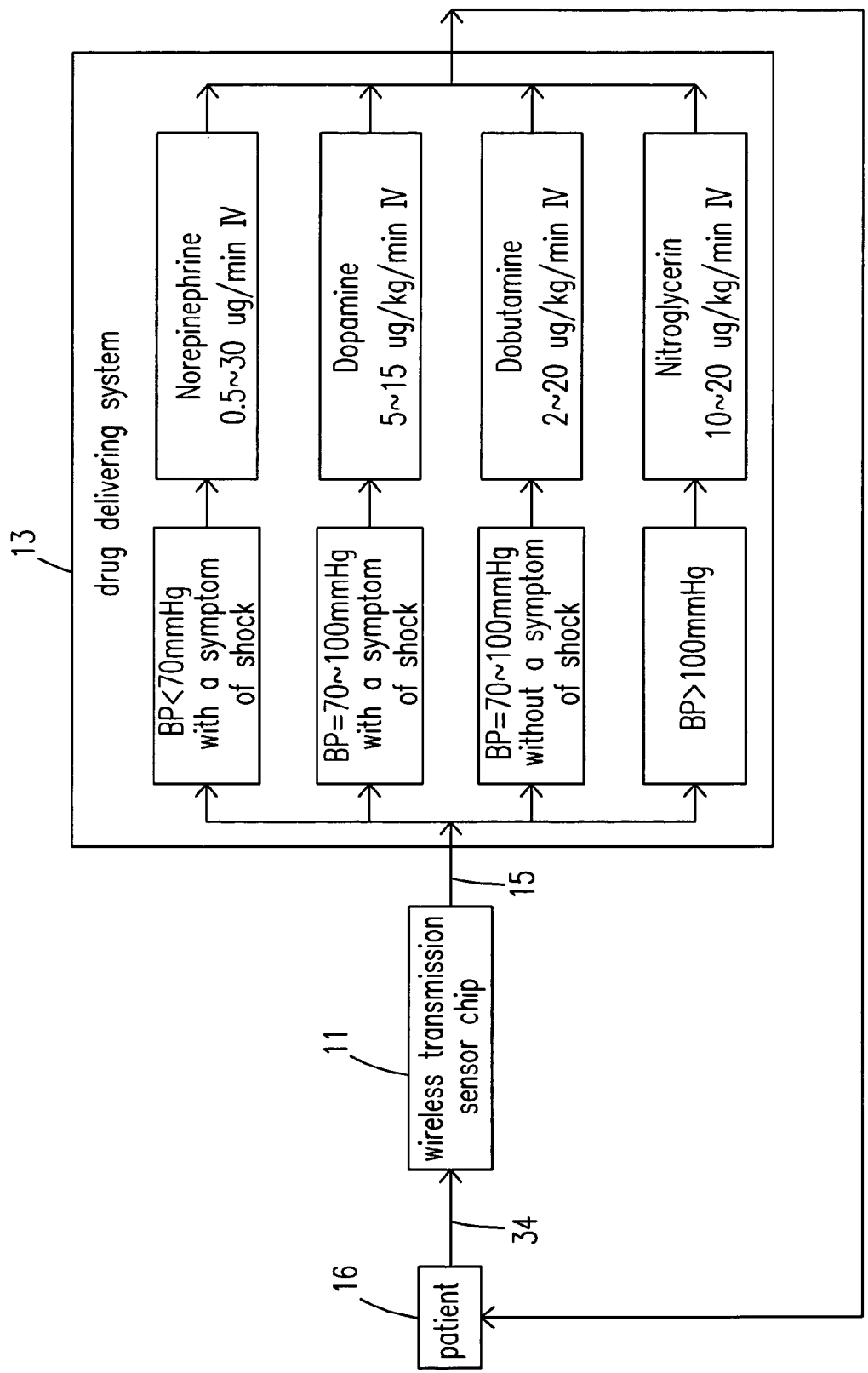
FIG. 4 is a flowchart showing the method of wireless physiological signal integration according to a preferred embodiment in the present invention.

Please refer to FIG. 4, which is a flowchart showing the method of wireless physiological signal integration according to a preferred embodiment in the present invention. As shown in FIG. 4, the wireless transmission sensor chip 11 senses a blood pressure (BP) 34 of a patient 16, converts the blood pressure 34 into a converted signal 15, and wirelessly transmits the converted signal 15 to a drug delivering system 13 for analyzing. The drug delivering system 13 determines the dose of a drug that the patient 16 needs, and automatically delivers the drug to the patient 16.

When the analyzed result shows that the patient 16 has the blood pressure lower than 70 mmHg with a symptom of shock, the drug delivering system 13 delivers 0.5-30 µg of Norepinephrine per minute through intravenous injection (IV). When the analyzed result shows that the patient 16 has the blood pressure equal to 70-100 mmHg with a symptom of shock, the drug delivering system 13 delivers 5-15 µg of Dopamine per kilogram body weight per minute through intravenous injection. When the analyzed result shows that the patient 16 has the blood pressure equal to 70-100 mmHg without a symptom of shock, the drug delivering system 13 delivers 2-20 µg of Dobutamine per kilogram body weight per minute through intravenous injection. When the analyzed result shows that the patient 16 has the blood pressure higher than 100 mmHg, the drug delivering system 13 delivers 10-20 µg of Nitroglycerin per kilogram body weight per minute through intravenous injection.

In conclusion, the present invention provides a system and method of wireless physiological signal integration for reducing the inconvenience of patients resulting from conducting wires. In addition, the wireless transmission sensor chip integrates and wirelessly transmits the detected physiological parameters, so that the physiological status of the patient can be monitored anytime, and it prevents the possible errors which may occur when writing the physiological parameters manually. The system and method provided by the present invention further comprises a drug delivering system to determine the dose and timing for providing a drug while monitoring the patient's physiological status, and the drug delivering system can delivers the drug to the patient automatically, so that the medication can be more precise and accurate. Accordingly, the present invention can effectively solve the problems and drawbacks in the prior art, and thus it fits the demand of the industry and is industrially valuable.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A system of a wireless physiological signal integration, comprising:
    a wireless transmission sensor chip, comprising:
        a sensor including a luminescent substance, a peroxidase, and a photodiode sensing a physiological signal of a patient, wherein the physiological signal includes a luminescence, and the peroxidase catalyzes a peroxide included in a sample obtained from the patient to react with the luminescent substance to generate the luminescence;
        a signal conversion module converting the physiological signal into a converted signal; and
        a wireless transmission module wirelessly transmitting the converted signal; and
    a drug delivering system determining a dose of a drug and a timing for providing the drug according to the converted signal.

2. A system according to claim 1, wherein the wireless transmission sensor chip is a System-on-Chip.

3. A system according to claim 1, wherein the wireless transmission sensor chip is fabricated by an integrated circuit process, and the integrated circuit process is a CMOS process.

4. A system according to claim 1, wherein the wireless transmission sensor chip is one of an invasive chip implanted in the patient and a non-invasive chip fastened at an exterior of the patient.

5. A system according to claim 1, wherein the wireless transmission sensor chip further comprises a plurality of sensors for sensing a plurality of physiological signals.

6. A system according to claim 1, wherein the sensor further includes a charge-induced transistor, a field effect transistor, an organic thin film transistor, and an ion selective electrode.

7. A system according to claim 1, wherein the sensor further comprises a reacting substance encapsulated by a sol-gel.

8. A system according to claim 1, wherein the physiological signal is one selected from a group consisting of an electrical signal, a chemical signal and a physical signal.

9. A system according to claim 8, wherein the sensor converts the physiological signal into a current and transmits the current to the signal conversion module when the physiological signal is one of the chemical signal and the physical signal, and the signal conversion module converts the current into an analog voltage and further converts the analog voltage into the converted signal, wherein the converted signal is an analog voltage signal.

10. A system according to claim 8, wherein when the physiological signal is the electrical signal, the signal conversion module converts the electrical signal into an analog voltage and further converts the analog voltage into the converted signal, and the converted signal is an analog voltage signal.

11. A system according to claim 1, wherein the physiological signal is one selected from a group consisting of a drug concentration, a DNA, an RNA, a protein, an ion, a blood sugar, a blood oxygen, a physiological substance, a brain wave, an electrocardiogram signal, a blood pressure, a pulse rate, a body temperature, and a light signal.

12. A system according to claim 1, further comprising a power supply electrically connected to the wireless transmission sensor chip for providing a power thereto, wherein the power supply is a battery.

13. A system according to claim 1, wherein the drug delivering system further comprises a wireless signal receiving module for receiving the converted signal.

14. A system according to claim 1, wherein the drug delivering system provides the drug to the patient automatically.

15. A system according to claim 1, wherein the drug delivering system delivers the drug to a body part of the patient.

* * * * *